United States Patent [19]
Christensen

[11] 3,971,248
[45] July 27, 1976

[54] UNIT FOR ASCERTAINING THE PRESENCE OF WATER IN LUBRICATING OIL

[76] Inventor: Arne Orskov Christensen, 14, Glentevej, DK-9900 Frederikshavn, Denmark

[22] Filed: Feb. 1, 1974

[21] Appl. No.: 438,655

[30] Foreign Application Priority Data
Dec. 14, 1973  Denmark .................. 6809/73

[52] U.S. Cl. .............................................. 73/61.1 R
[51] Int. Cl.² ............... G01N 25/14; G01N 33/26
[58] Field of Search ............ 73/53, 61.1 R, 61.3, 73/64, 17 A, 76; 203/12; 184/6.4; 200/61.05, 61.4; 340/235

[56] References Cited
UNITED STATES PATENTS
1,307,601  6/1919  Saunders .................. 73/17 A X
3,203,227  8/1965  Donnell ...................... 73/17 A
3,311,722  3/1967  Hammerschmidt et al. ...... 200/61.05

FOREIGN PATENTS OR APPLICATIONS
7,477  10/1879  Germany .................. 73/61.1 R Primary Examiner—James J. Gill

[57] ABSTRACT

A unit for ascertaining the presence of water in lubricating oil, comprising a condensing chamber communicating with a heating chamber for the heating of lubricating oil, said condensing chamber being provided with a condensing surface, and means to ascertain a quantity of condensate collected by means of the condensing surface.

6 Claims, 3 Drawing Figures

UNIT FOR ASCERTAINING THE PRESENCE OF WATER IN LUBRICATING OIL

The invention relates to a unit for ascertaining the presence of water in lubricating oil.

Ascertaining the presence of water in lubricating oil is of great importance in connection with machinery, especially in connection marine engines where considerable damage may occur as a consequence of poor lubrication.

In the following the invention will be explained in detail in connection with the lubricating of marine engines. As a rule, in such engines water is used for cooling the engine cylinders or the lubricating oil, and a leakage may cause water to seep into the lubricating system of the engine.

Most frequently this happens when the engine is stopped, because then there is no counter-pressure from the oil to keep out the water, and the water will collect at the bottom of the oil pan of the engine or of a separate lubricating oil tank, separated from the oil which will float on the water.

It is the object of the inventon in a simple and dependable manner to ascertain the presence of water in lubricating oil pumped from e.g. an oil pan or a lubricating-oil tank.

According to the invention this is obtained by the fact that the unit comprises a condensing chamber communicating with a heating chamber for heating lubricating oil, said condensing chamber being provided with a condensing surface, and means to ascertain condensate collected by means of said condensing surface.

The unit has proved highly reliable in ascertaining critical water contents, so that the operating crew will be warned.

According to the invention the heating chamber and the condensing chamber may be located in a common housing, the heating chamber constituting the lower portion, and the condensing chamber the upper portion of the housing. This arrangement provides a compact and dependable unit. According to the invention a perforated partition wall may be located between the two chambers, e.g. a perforated plate or a net detaining oil particles, if any, in the heating chamber.

According to the invention the condensing surface may define a coolant-containing chamber having an inlet and an outlet for coolant, and the said chamber may be connected to a pump for sea water, which in many cases will suffice as cooling medium.

According to the invention the coolant-containing chamber may also consist of an oil chamber having an inlet for the oil to be examined, and an outlet for the oil to the heating chamber.

This means first that the oil to be examined for its content of water, prior to the examination is used as cooling medium for the condensing surface, and second that by this means in a simple way a pre-condition is established for providing in the oil supply line to the heating chamber a balancing chamber for balancing fluctuations in the oil supply, the oil chamber according to a preferred embodiment of the invention being dimensioned as such a balancing chamber. In this way it is possible e.g. to balance pressure fluctuations in the supply pipes for oil to engines, fluctuations depending on the working of the engine, the pressure being high e.g. in case of a cold start when the oil is still cold. The arrangement according to the invention ensures a fairly constant temperature, e.g. an average temperature of the oil of about 50°C and a temperature in the heating chamber of about 120°C. Also the risk of ruining the coolant-containing chamber by corrosion is eliminated.

According to the invention the eondensing surface may incline to a horizontal plane, the collection of condensate precipitated on the surface thus being facilitated. According to the invention it is particularly advantageous to shape the condensing surface as an inverted cone for the collection of the condensate.

According to the invention the collected condensate may be received in a collecting member located at the lowermost end of the cooling surface. If the condensing surface is cone-shaped the top of the cone may be provided with a downwardly extending tip projecting towards or into the collecting member, thus ensuring a safe transfer of condensate from the condensing surface to the collecting member. The cone-shape of the condensing surface is an embodiment ensuring the collection of condensate, even if the sea is rough.

For measuring the quantity of collected condensate the unit according to the invention may comprise a measuring device containing a measuring chamber provided with measuring members for ascertaining the presence of a predetermined quantity of condensate in the chamber. This means that the unit does not warn the operators until a critical quantity of water has been ascertained, while negligible quantities of water are disregarded.

According to the invention the measuring members may be connected to alarm members automatically giving the alarm when a critical water threshold is reached. For this purpose the measuring members according to the invention may consist of two electrodes located so as to shortcircuit when the water reaches a predetermined quantity.

According to the invention a fore-chamber may be arranged in the condensate conduit to the measuring chamber, said fore-chamber collecting a predetermined quantity of condensate before passing it on to the measuring chamber. Thus, particularly reliable working conditions are created, and the arrangement also ensures good ventilation which counteracts the risk of explosions.

For the purpose of reliable operation the measuring chamber or the fore-chamber or both may be provided with an outlet member in the form of a syphon.

According to the invention, the electrode placed at a lower level than the other electrode may be shaped like a vessel or extend into a vessel dimensioned so as to receive a quantity of water from the fore-chamber and provided with a bottom outlet so dimensioned that the vessel can be emptied gradually through the outlet, the other electrode being located at the upper end of the vessel. The measuring operation now proceeds in the way that a quantity of water from the fore-chamber is transferred to the said vessel and fills it, the presence of water being instantly ascertained by the shortcircuiting of the electrodes. Until another quantity of water is collected, the quantity transferred to the vessel will gradually be discharged through the bottom outlet of the vessel. In this way and by means of a simple and dependable device the required measurements will be carried out with great precision.

Finally, an outlet from the measuring chamber may discharge into an additional chamber for measuring a quantity of condensate per unit of time. Thus, in addition to ascertaining a critical quantity of water in the measuring chamber which may already give the alarm, e.g. a preliminary alarm, also the speed at which the water increases to the critical value may be measured. This measuring may result in an additional serious alarm, and to this end according to the invention the additional measuring chamber may be connected to alarm members starting to operate when the condensate has reached a predetermined quantity also in the measuring chamber.

The unit described in the above will primarily be used when the engine works. However, according to the invention the unit may also comprise means for ascertaining the presence of water before the engine is started, so that water conditions can be watched at all stages of operation.

To this purpose the unit according to the invention may comprise a device arranged in the supply line for lubricating oil to the unit, said device being adapted for the observation of the nature of the medium supplied to the unit, so that before the engine is started it becomes possible visually to ascertain whether lubricating oil or water is pumped from the oil pan or the lubricating-oil tank.

According to the invention, in addition to a sight glass the observation device may comprise detectors reacting to the presence of pure water and connected to warning members, the reliability of working conditions being increased by automatic warning, if visual inspection should fail.

According to the invention the observation device may be connected to an oil-feed pipe for the unit by means of a change-over valve normally establishing the connection with the unit. This means that the ascertaining means first described will always be coupled to the lubricating-oil supply, unless the observation device has been engaged by operation of the change-over valve before the engine is started.

The invention will now be explained in more detail, reference being had to the drawing.

Figure 1:
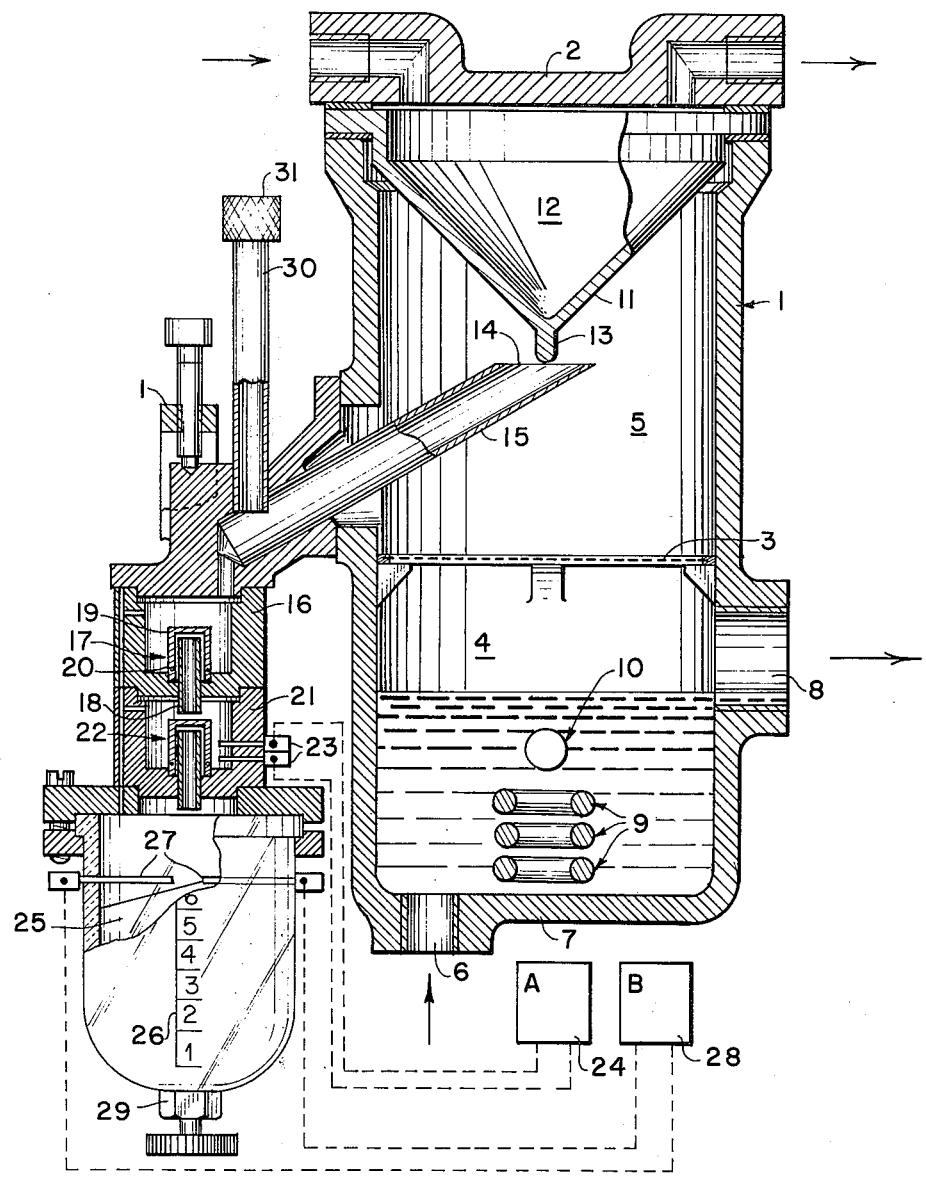
FIG. 1 is a schematic embodiment of the unit according to the invention.

The unit comprises a cylindrical, vertical housing 1 closed at the top by means of a detachable cover 2. By means of a perforated plate or net 3 the housing is divided into a lower heating chamber 4 for lubricating oil and an upper condensing chamber 5 for aqueous vapour. The lubricating oil is fed to the heating chamber 4 through an inlet 6 in the bottom 7 of the housing and is discharged from the chamber through an outlet 8 in the lateral wall of the housing. The chamber 4 also contains thermostatically controlled heating elements 9 and a thermostat phial 10, all located below the level of the outlet 8.

A condensing surface shaped as an inverted cone 11 is provided in the upper part of the condensing chamber 5, said surface defining a chamber 12 containing coolant, which in a conventional manner, not shown in detail, is connected with an inlet and an outlet for coolant. The cooling medium may e.g. be sea water fed by means of a pump. The lower end of the inverted cone is provided with a downwardly extending tip 13 terminating at the inlet 14 of a tubular collecting member 15 slanting downwards through the side wall of the housing 1. The tip 13 may also project to some extent into the collecting member 15.

The collecting member 15 discharges into a measuring device which in the present example comprises a fore-chamber, a measuring chamber and an additional measuring chamber. The collecting member discharges into the fore-chamber 16 which by means of a syphon 17 consisting of an open ended tube 18 and a shell 19 in the form of inlet inverted container surrounding the tube with clearance and having inelt apertures 20 in proximity to its lowermost edge, communicates with the measuring chamber 21 which has an outlet in the form of a syphon 22 similar to the syphon 17. The measuring chamber 21 contains measuring members in the form of two electrodes 23 for ascertaining the presence of a predetermined quantity of condensate in the chamber 21, the electrodes being so placed that they are short-circuited when the water level in the chamber 21 reaches a predetermined height. The electrodes 23 are connected to warning members 24, e.g. a yellow signal light.

The syphon 22 connects the measuring chamber 21 with an additional measuring chamber 25 consisting of a sight glass with a measuring scale 26, by means of which an incoming quantity of fluid can be measured per unit of time. Electrodes 27 are located in the upper part of the measuring chamber 25 and are short-circuited when the fluid in the measuring chamber 25 reaches maximum height. The electrodes 27 are connected to warning members 28, e.g. a red signal light supplemented with an accoustic signal if desired.

At its bottom the additional measuring chamber 25 has a conventional drain 29.

The apparatus operates in the following way.

Through the inlet 6 lubricating oil is supplied to the heating chamber 4 where it is heated to e.g. app. 55°C by means of the heating elements 9. If during operation the lubricating oil is sufficiently heated in another way, e.g. by means of engine heat, the heating elements 9 can be disconnected by means of the thermostat phial 10.

When the oil is heated, water which may be present in the oil is separated therefrom as an aqueous vapour passing through the plate or net 3 which will keep back oil particles, if any, and rising towards the cooled condensation cone 11. When touching the cold outer surface of the cone the vapour condenses and the condensate runs down along the conical surface and is collected at the lower end of the inverted cone, whereupon it runs down along the tip 13 and into the collecting tube 15 conveying the condensate to the fore-chamber 16.

When condensate continues to run down, the fore-chamber 16 will gradually be filled to a height at which the syphon 17 starts functioning, transferring the condensate collected in the chamber to the measuring chamber 21. In the shown embodiment the chambers 16 and 21 have the same volume, which means that the electrodes 23 are short-circuited as soon as the condensate is transferred from the chamber 16 to the chamber 21. The short-circuiting of the electrodes 23 may e.g. cause a yellow signal light to be lit as a preliminary warning that the lubricating oil contains water.

The signal light is not turned off until the syphon 22 starts functioning and takes the condensate from the measuring chamber 21 into the additional measuring chamber 25. This additional chamber has a substantially larger capacity than the measuring chamber 21 and can therefore be so arranged that the electrodes 23 of the measuring chamber 21 besides being connected to the warning members 24 are also connected to recording members in the form of e.g. a counter and possibly also a time indicator, so that it can be ascertained how many times the syphon 22 works within a predetermined period of time.

When the condensate has filled the additional measuring chamber 25 to such a degree that the electrodes 27 are short-circuited, the warning members 28 are activated and indicate that the water content has now reached a critical value.

The collecting pipe 15 is coupled to an upstanding ventilating pipe 30 with a safety net 31 through which oil vapour, if any, can be discharged.

Figure 2:
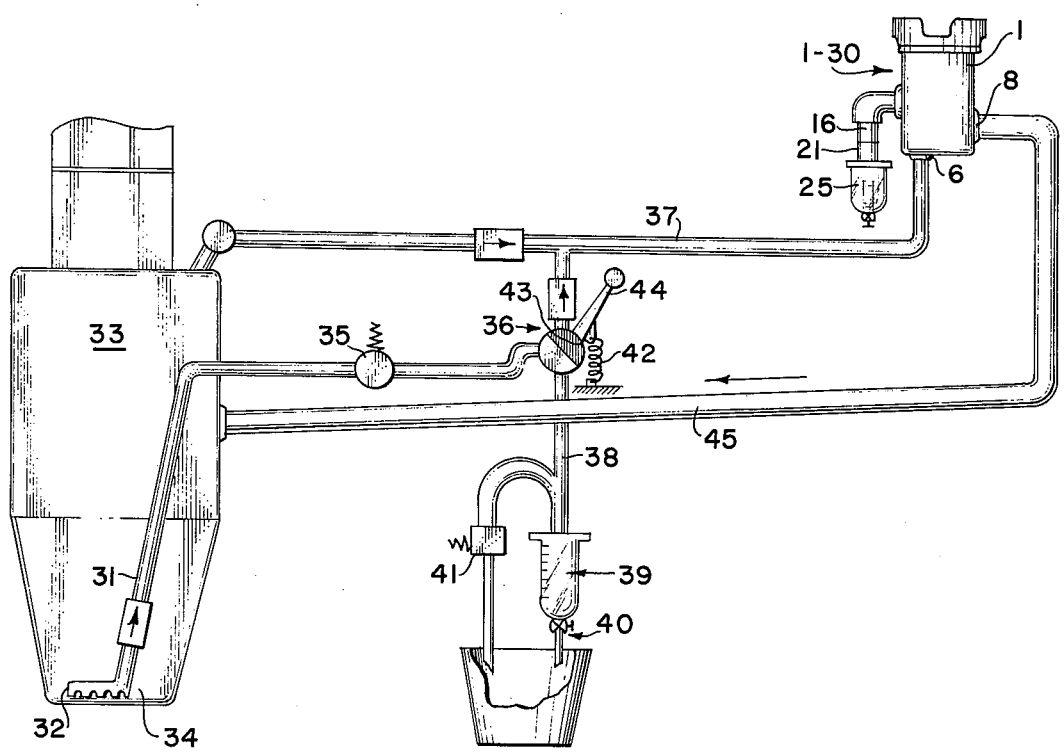
FIG. 2 shows a unit provided with an observation device.

In the embodiment shown in FIG. 2 the unit 1–30 heretofore described is supplemented with an additional device for visual observation of the flow of medium in order to see whether it is a water or oil flow.

The device comprises a suction pipe 31 with a rose box 32 located at the lowermost point of e.g. the oil pan 34 of an engine 33 or of a lubricating-oil tank. A pump 35 is coupled in the pipe 31, and the pipe ends in a conventional change-over valve 36 which via a pipe 37 connects the pipe 31 with the inlet 6, and via a pipe 38 connects the pipe 31 with a sight glass 39. If desired, the sight glass 39 may contain electrodes similar to the electrodes 23 to ascertain whether the fluid pumped into the glass is pure water. The sight glass 39 is at its lower end provided with a conventional drain 40 and connected with a conventional relief valve 41.

By means of a tension spring 42 the cock plug 43 of the change-over valve 36 is normally held in a position wherein the valve connects the pipe 31 with the pipe 37, the said spring pulling a handle 44 connected with the cock plug 43.

The device works as follows.

The pump 35 is started before the engine is started, and at the same time by lifting of the valve handle 44 the change-over valve is so adjusted that the flow of medium is directed to the sight glass 39. It is now possible readily to ascertain by sight and also by electric means, if any, whether the pumped medium is water or oil, and this control can be carried out without any need for starting any of the pumps belonging to the engine. These pumps might soon mix water, if any, with the oil with the result that the water pumped forward might already have caused damage to the bearings.

After the pre-control the handle 44 can be released, whereupon the spring 42 pulls the cock plug 43 into a position where it connects the pipe 31 with the pipe 37, thus engaging the unit 1–30.

If so desired, the pre-control may be coupled to the starting device of the engine so that it becomes necessary to carry out the pre-control before the engine can start.

The pre-control can also be carried out by placing the electrodes at the points which one wishes to control so that various measuring points may be tested by means of a selector switch and by means of the same amplifying and warning device.

In combination with the unit 1–30 the apparatus 31–44 ensures an effective control of the condition of the lubricating oil, the control starting before the engine is started, and continuing with a constant watch during the operation of the engine, so that complete security can be obtained against breakdowns on account of the presence of water in the lubricating oil.

Finally, the unit 1–30 may also be utilized for removing detrimental water from the lubricating oil, because the outlet 8 — as shown in FIG. 2 — can be connected with the oil pan 34 or the oil tank by means of a return pipe 45 returning the lubricating oil from the chamber 4 where the oil was relieved of water, to the oilpan or the tank.

The pump 35 may be stopped and started by means of a pressure control in the oil pipe of the engine.

Figure 3:
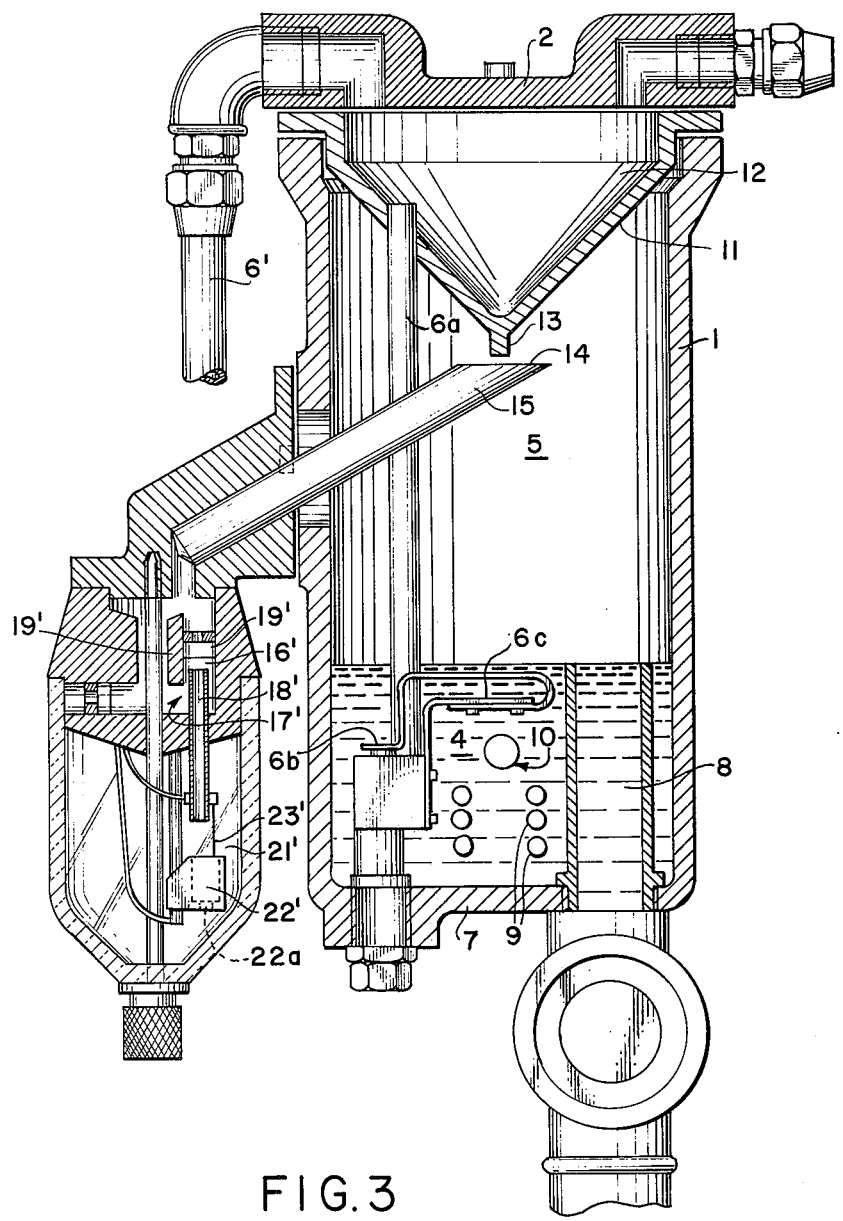
FIG. 3 is another embodiment of the unit according to the invention.

The unit according to FIG. 3 also comprises a cylindrical upstanding housing 1, which at its top is closed by means of a detachable cover 2. The lower part of the housing is a heating chamber 4 for oil and the upper part a condensing chamber 5 for aqueous vapour. The oil is supplied through an inlet 6'. The bottom 7 of the housing has an oil outlet 8. This outlet is formed as an overflow. Further, the chamber 4 contains thermostatically controlled heating elements 9 and a thermostat phial 10, all placed below the level of the outlet 8.

A condensing surface in the form of an inverted cone 11 is provided in the upper part of the condensing chamber 5, said cone defining a chamber 12 containing coolant. The inlet 6' discharges at the top of said chamber, and the chamber communicates with the heating chamber 4 by means of a tube 6a, the upper end of the tube entering the cone 11 up in the wall. At its lower end the tube is closed by means of a valve 6b which can also be opened by means of a heat detector 6c located in the chamber 4, if the temperature of the oil in the chamber 4 should exceed a predetermined limit, so that the oil in the chamber 4 can be cooled by admission of cool oil.

The lower end of the inverted cone is provided with a downwardly extending tip 13 terminating at the inlet 14 of a tubular collecting member 15 which slants downwards out through the side wall of the housing 1. The tip 13 may also project to some extent into the collecting member 15.

The collecting member 15 discharges into a measuring device containing a fore-chamber 16' and a measuring chamber 21'. The collecting member discharges into the fore-chamber 16' which communicates with the measuring chamber 21' by means of a syphon 17' consisting of an open tube 18' and a part of the wall 19' of the chamber surrounding the tube with clearance.

The measuring chamber 21' contains measuring members in the form of two electrodes 22' and 23' to ascertain the presence of a predetermined quantity of condensate in the chamber 21'. The electrode 22' placed at a lower level than the electrode 23' is a vessel, whereas the electrode 23' is located at the upper end of the said vessel. The vessel is dimensioned to receive a quantity of water from the fore-chamber 16' and provided with a bottom outlet 22a so dimensioned that the vessel can be gradually emptied through the outlet.

The electrodes 22' and 23' are placed so as to be short-circuited when the level of water in the chamber 21' reaches a predetermined height. The electrodes 22' and 23' are connected with warning members not shown, e.g. a yellow signal light.

The unit operates in the following way.

Through the inlet 6', the chamber 12 and the tube 6a oil is supplied to the heating chamber 4, where by means of the heating elements 9 the oil is heated to e.g. about 120°C. If a predetermined temperature is reached the heating elements 9 will be disconnected by means of the thermostat phial 10.

By heating the oil any water contained in the oil is separated as an aqueous vapour rising towards the cooled condensing cone 11. When touching the cold outer surface of the cone the vapour condenses, and the condensate runs down along the surface of the cone and is collected at the lower end of the inverted cone, from where it runs down along the tip 13 and into the collecting tube 15 conveying the condensate to the fore-chamber 16'.

When condensate continues to run down, the fore-chamber 16' will gradually be filled to a height at which the syphon 17' starts functioning transferring a quantity of condensate to the measuring chamber 21', so that the vessel electrode 22' is filled. Hereby the electrodes 22' and 23' are short-circuited. The short-circuiting causes e.g. a yellow signal light to be turned on as a preliminary warning that water has been ascertained in the lubricating oil.

The unit according to the invention may also be used for controlling the presence of water in oil other than lubricating oil.

I claim:

1. An apparatus for ascertaining the presence of water in an oil, comprising a condensing chamber, a heating chamber for heating said oil, said two chambers communicating with each other, the condensing chamber being provided with a condensing surface, the condensing surface having a discharge end adapted to collect the condensate at a predetermined location by means of gravity, a measuring chamber for ascertaining the presence of a predetermined quantity of condensate in the chamber, communicating means adapted to feed the condensate collected at the discharge end of the condensing surface to the measuring chamber, the measuring chamber being provided with warning means adapted to emit a warning signal when the water in the measuring chamber reaches a predetermined quantity and a fore-chamber provided between the communicating means and the measuring chamber, the communicating means discharging into the fore-chamber, the fore-chamber being adapted to collect a predetermined quantity of condensate and provided with outlet means for delivering the quantity thus collected as a whole into the measuring chamber.

2. An apparatus according to claim 1, in which the condensing surface is in the form of an inverted cone.

3. An apparatus according to claim 2, in which the inverted cone at its end is provided with a downwardly extending tip projecting towards the communicating means.

4. An apparatus according to claim 1, wherein said condensing surface is in contact with a coolant-containing chamber comprising an oil chamber having an inlet for the oil to be examined and an outlet for the oil to the heating chamber.

5. An apparatus according to claim 4, in which the oil chamber is adapted to communicate with a lubricating system and dimensioned as an equalizing chamber to balance fluctuations in the oil supply.

6. An apparatus according to claim 1, wherein the measuring chamber is provided with at least two electrodes so located that they are short-circuited when the water reaches a predetermined quantity, the electrodes being located at different levels, the lowermost electrode being adapted to project into a vessel which is dimensioned so as to receive a predetermined charge of water and provided with a bottom outlet so dimensioned that the vessel can be gradually emptied through the outlet, the other electrode being located at the upper end of the vessel.

* * * * *